(12) United States Patent
Mahoney, Jr. et al.

(10) Patent No.: US 11,253,349 B2
(45) Date of Patent: Feb. 22, 2022

(54) METHODS AND DEVICES FOR TENSIONING GRAFTS

(71) Applicant: Medos International Sarl, LeLocle (CH)

(72) Inventors: James J. Mahoney, Jr., Hyde Park, MA (US); Nathaniel H. Henderson, Westport, MA (US); Kevin John Zylka, Fort Wayne, IN (US); Jacob A. Marks, Mansfield, MA (US); Arthur Stephen, Raynham, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 317 days.

(21) Appl. No.: 16/352,354

(22) Filed: Mar. 13, 2019

(65) Prior Publication Data

US 2019/0209286 A1 Jul. 11, 2019

Related U.S. Application Data

(62) Division of application No. 15/198,189, filed on Jun. 30, 2016, now Pat. No. 10,265,157.

(51) Int. Cl.
*A61F 2/08* (2006.01)
*A61B 17/04* (2006.01)
*A61B 90/00* (2016.01)

(52) U.S. Cl.
CPC ........ *A61F 2/0805* (2013.01); *A61B 17/0401* (2013.01); *A61F 2/0811* (2013.01); *A61B 2017/0496* (2013.01); *A61B 2090/064* (2016.02)

(58) Field of Classification Search
CPC ...... A61B 2017/0496; A61B 2017/081; A61B 2017/086; A61B 17/1327; A61B 17/30;
(Continued)

(56) References Cited

U.S. PATENT DOCUMENTS

| 4,712,542 A | 12/1987 | Daniel et al. |
| RE34,762 E | 10/1994 | Goble et al. |

(Continued)

FOREIGN PATENT DOCUMENTS

| WO | WO-2008002550 A2 | 1/2008 |
| WO | WO-2012158583 A1 | 11/2012 |

OTHER PUBLICATIONS

European Search Report for Application No. 17178763.3 dated Nov. 23, 2017.

*Primary Examiner* — Wade Miles
*Assistant Examiner* — Mikail A Mannan

(57) ABSTRACT

Various exemplary methods and devices for tensioning grafts are provided. In general, a surgical device can include a grip and a frame. The frame can have two opposed segments. The segments can be spaced apart from one another and can each be configured to have at least one suture attached thereto. The sutures attached to the frame can each be configured to attach to a graft. The two segments can be configured to dynamically move toward and away from each other in response to tension that is applied to the sutures attached to the frame. The frame can include an indicator configured to provide an indication of the tension applied to the sutures. The grip can have at least one opening therein. The at least one opening can be configured to have a surgical instrument passed therethrough.

14 Claims, 7 Drawing Sheets

(58) Field of Classification Search
CPC ... A61B 17/0487; A61B 17/08; A61B 17/122; A61B 17/0466; A61B 17/0401; A61B 2090/064; A61F 2/0805; A61F 2/0811; A61F 2/08; A61F 2/083; A61F 2/122; A61F 2/1227

See application file for complete search history.

(56) References Cited

U.S. PATENT DOCUMENTS

| | | | |
|---|---|---|---|
| 5,507,750 | A | 4/1996 | Goble et al. |
| 5,630,820 | A | 5/1997 | Todd |
| 5,649,940 | A | 7/1997 | Hart et al. |
| 5,690,655 | A | 11/1997 | Hart et al. |
| 5,713,897 | A | 2/1998 | Goble et al. |
| 5,980,473 | A | 11/1999 | Korakianitis et al. |
| 6,001,106 | A | 12/1999 | Ryan et al. |
| 6,547,778 | B1 * | 4/2003 | Sklar .......... A61F 2/08 606/1 |
| 6,554,862 | B2 | 4/2003 | Hays et al. |
| 6,679,889 | B1 | 1/2004 | West, Jr. et al. |
| 6,758,850 | B2 | 7/2004 | Smith et al. |
| 6,761,722 | B2 | 7/2004 | Cole et al. |
| 6,949,102 | B2 | 9/2005 | Andrews |
| 7,118,578 | B2 | 10/2006 | West, Jr. et al. |
| 7,160,285 | B2 | 1/2007 | Sklar et al. |
| 7,326,222 | B2 | 2/2008 | Dreyfuss et al. |
| 7,686,810 | B2 | 3/2010 | West, Jr. et al. |
| 8,123,806 | B1 | 2/2012 | Hoof |
| 8,182,495 | B2 | 5/2012 | DiStefano et al. |
| 8,197,485 | B2 | 6/2012 | Marshall et al. |
| 8,226,714 | B2 | 7/2012 | Beck, Jr. et al. |
| 8,298,247 | B2 | 10/2012 | Sterrett et al. |
| 8,317,806 | B2 | 11/2012 | Coe et al. |
| 8,435,293 | B2 | 5/2013 | Donnelly et al. |
| 8,540,734 | B2 | 9/2013 | Hoof |
| 8,657,880 | B2 | 2/2014 | Paulos |
| 8,679,122 | B2 | 3/2014 | Bernstein et al. |
| 8,790,357 | B1 | 7/2014 | Hoof |
| 8,888,791 | B2 | 11/2014 | Jaramillo et al. |
| 8,939,999 | B2 | 1/2015 | Sterrett et al. |
| 10,265,157 | B2 | 4/2019 | Mahoney, Jr. et al. |
| 2005/0049598 | A1 | 3/2005 | West et al. |
| 2005/0256527 | A1 | 11/2005 | Delfosse et al. |
| 2007/0198036 | A1 | 8/2007 | Sklar et al. |
| 2008/0033549 | A1 * | 2/2008 | Marshall .......... A61F 2/0805 623/13.13 |
| 2009/0202387 | A1 | 8/2009 | Dlugos, Jr. et al. |
| 2011/0009885 | A1 | 1/2011 | Graf et al. |
| 2011/0184438 | A1 | 7/2011 | Hoof |
| 2012/0158013 | A1 | 6/2012 | Stefanchik et al. |
| 2013/0245653 | A1 | 9/2013 | Litherland |
| 2015/0080902 | A1 | 3/2015 | Jaramillo et al. |
| 2017/0049517 | A1 | 2/2017 | Felder et al. |

\* cited by examiner

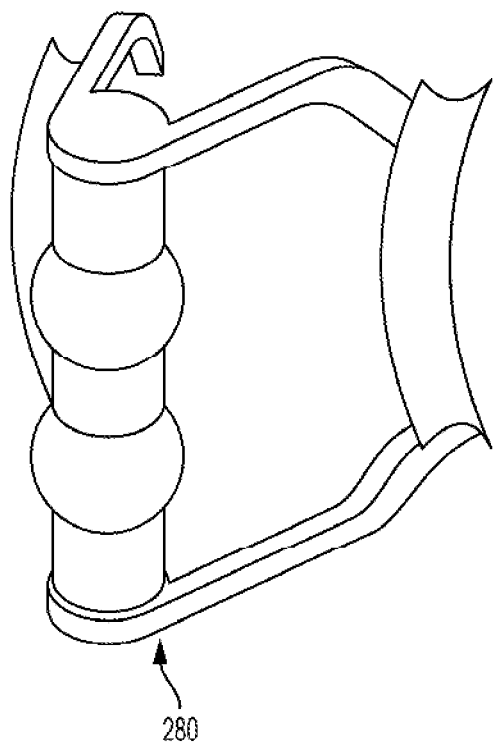
FIG. 18
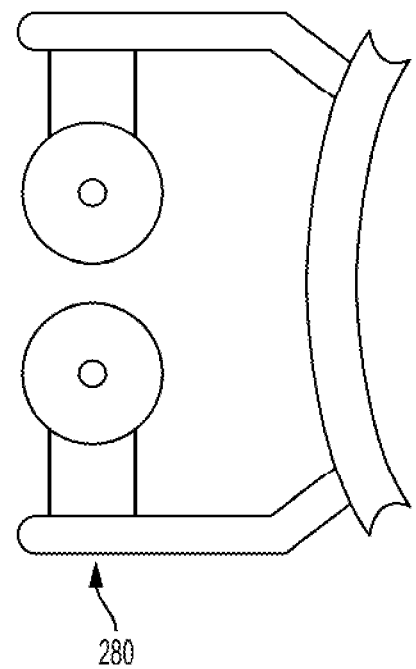
FIG. 19
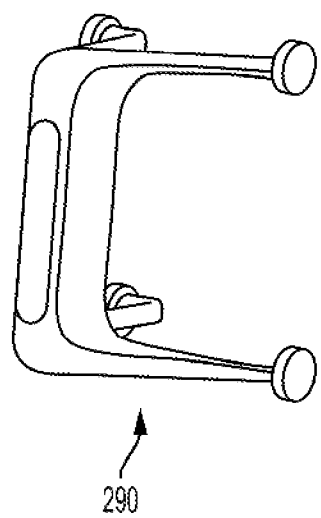
FIG. 20
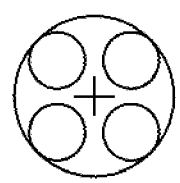    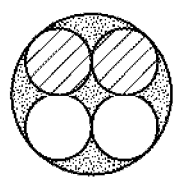
FIG. 21A    FIG. 21B
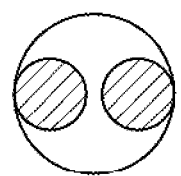    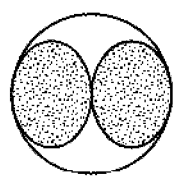
FIG. 21C    FIG. 21D

METHODS AND DEVICES FOR TENSIONING GRAFTS

CROSS REFERENCE TO RELATED APPLICATIONS

The present application is a divisional of U.S. patent application Ser. No. 15/198,189 entitled "Methods and Devices for Tensioning Grafts" filed Jun. 30, 2016, which is hereby incorporated by reference in its entirety.

BACKGROUND

During various procedures performed on ligaments, for example in reconstruction of the anterior cruciate ligament (ACL), it is often necessary to use grafts that can include a number of strands. For example, during an ACL reconstruction, four combined strands are often used, such as two (doubled) gracilis strands and two (doubled) semitendinosus strands. During other procedures performed on ACLs or other ligaments, other grafts can be used instead or in addition, such as patellar tendon, quadriceps tendon, tibialis, and the like. During procedures when more than one strand is used, the multiple graft strands are typically equally tensioned, meaning that the strands are under equal tension, in order to provide optimum biomechanical properties. The tension on each graft strand may be applied by hand one strand at a time, but this approach can make it difficult to achieve equal load on the various strands, can be time consuming, and/or can be challenging to perform. Various other approaches have been taken to apply equal tension, for example by applying weights to each strand or by using various hand-held devices, but these approaches can be time consuming, awkward, and/or laborious.

Accordingly, there remains a need for improved methods and devices for tensioning grafts.

SUMMARY

In general, methods and devices for tensioning grafts are provided.

In one aspect, a surgical device is provided that in one embodiment includes a grip configured to be held by a user, a frame formed of opposed first and second segments, and at least one suture retention mechanism formed on each of the first and second frame segments. The grip includes a passageway therein configured to allow passage of a surgical instrument therethrough with the grip being held by the user. The first and second segments are connected to each other and to the grip at one end by a flexure and being separated at an opposite end by a variable angle. The first and second frame segments are configured to move toward each other to decrease the variable angle in response to tension applied to a suture attached to the at least one suture retention mechanism.

The surgical device can vary in any number of ways. For example, the device can include an indicator configured to provide an indication of the tension applied to the suture. The indicator can include first and second indicators, and a relative positioning of the first indicator and the second indicator can provide an indication of the tension applied to the suture. The first indicator can include a mark on one of the first and second segments, and the second indicator can include a window in the other of the first and second segments. In at least some embodiments, the indicator can be visible through the passageway.

For another example, the flexure can include a living hinge.

For yet another example, the passageway can include at least one enclosed hole.

For still another example, the passageway can include at least one cut-out in a sidewall of the grip.

In another aspect, a surgical system is provided that in one embodiment includes a frame having a first portion and a second portion, and a grip having an aperture therethrough configured to allow passage of a surgical instrument. The first portion and the second portion each extend distally from the grip and each have proximal and distal ends. The proximal ends of the first portion and the second portion are coupled to the grip by a plurality of hinges. The distal ends of the first portion and the second portion are moveably spaced apart from each other. The first portion and the second portion each have at least one suture retention mechanism coupled thereto, The frame is movable between a first position, in which the plurality of hinges biases the distal ends of the first and second portions away from each other, and a second position, in which the distal ends of the first and second portions have moved toward each other in response to a force applied to the frame to overcome the bias.

The system can have any number of variations. For example, the system can include an indicator configured to provide an indication of the force applied to the frame. The system can also include a surgical instrument passed through the aperture, and the indicator can be visible when the surgical instrument is extended therethrough. Alternatively or additionally, the indicator can include first and second indicators, and a position of the first indicator and the second indicator relative to each other can provide the indication of the force applied to the frame.

For another example, each of the plurality of hinges includes a living hinge.

For yet another example, the system can include a plurality of sutures. Each of the sutures can be configured to be removably secured to the at least one suture retention mechanism. With the plurality of sutures removably secured to the at least one suture retention mechanism, the plurality of sutures can be configured to be at a first tension with the frame in the first position and to be at a second, greater tension with the frame in the second position. The frame can include an indicator configured to indicate that the plurality of sutures have achieved the second tension in response to the movement of the frame from the first position to the second position.

In another aspect, a surgical method is provides that in one embodiment includes coupling a plurality of graft strands to a plurality of suture retention members of a graft tensioning device. The plurality of graft strands are at a first tension when coupled to the graft tensioning device. The method also includes applying a tension force to the graft strands through the tensioning device. The tension force causes the plurality of graft strands to change from being at the first tension to being at a second tension. The graft tensioning device includes an indicator that indicates that the plurality of graft strands are at the second tension.

The method can have any number of variations. For example, applying the tension force can cause first and second segments of the tensioning device to dynamically flex at a flexure coupling the first and second segments together. For another example, the indicator can be configured to indicate any one of a plurality of predetermined tensions, and the second tension can be one of the predetermined tensions. For yet another example, the method can include advancing a surgical instrument through a passageway of the graft tensioning device.

BRIEF DESCRIPTION OF DRAWINGS

This invention will be more fully understood from the following detailed description taken in conjunction with the accompanying drawings, in which:

FIG. 18 is a perspective view of still another embodiment of a tensioning device;

FIG. 19 is a side view of the device of FIG. 18;

FIG. 20 is a perspective view of yet another embodiment of a tensioning device;

FIG. 21A is a top view of one embodiment of four graft strands before tensioning;

FIG. 21B is a top view of the four graft stands of FIG. 21A after tensioning thereof;

FIG. 21C is a top view of one embodiment of two graft strands before tensioning; and FIG. 21D is a top view of the two graft stands of FIG. 21C after tensioning thereof.

DETAILED DESCRIPTION

Figure 1:
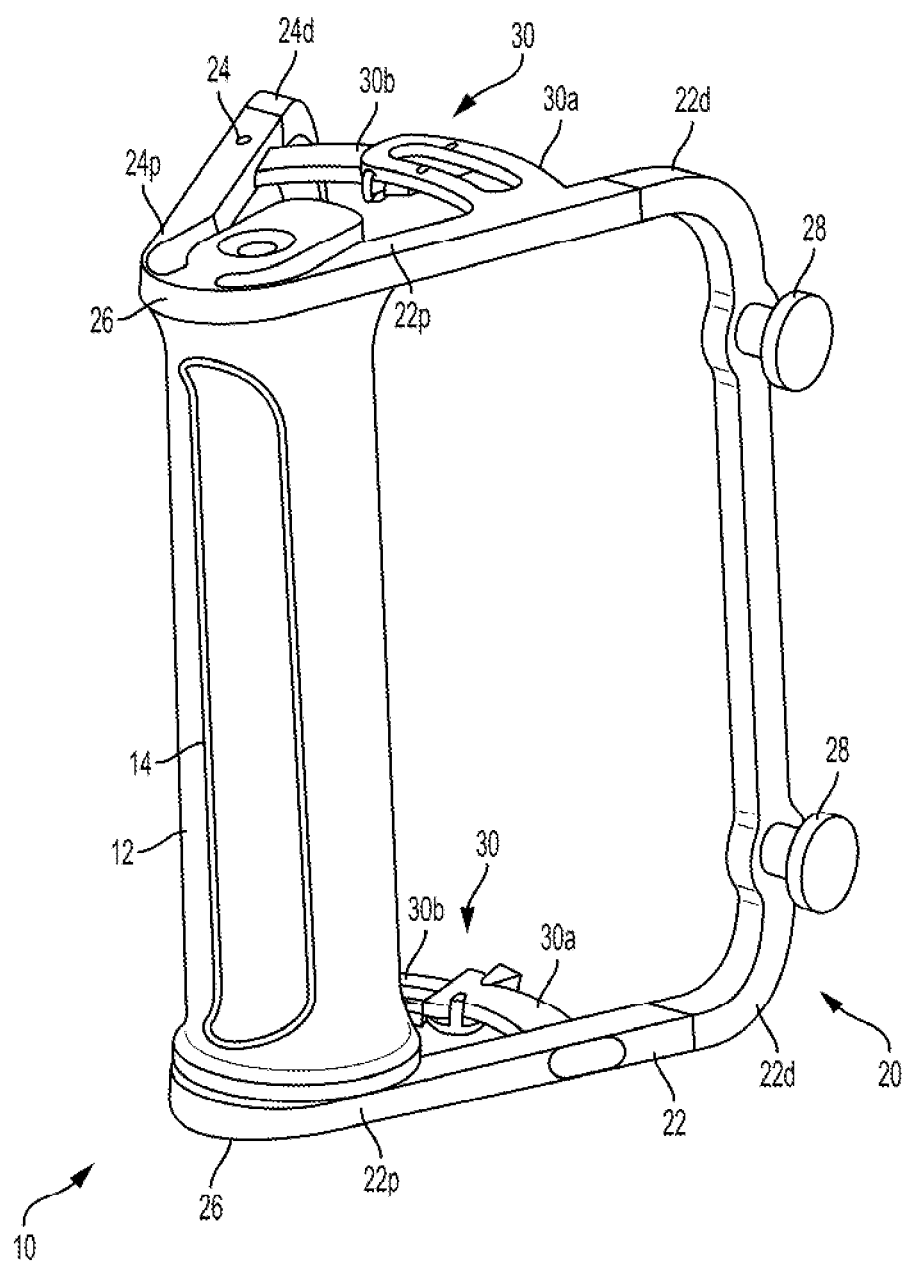
FIG. 1 is a perspective view of one embodiment of a tensioning device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices for tensioning grafts are provided. In general, a surgical device includes a grip and a frame. The frame has two opposed segments, which are spaced apart from one another and each of which is configured to have at least one suture attached thereto. The two segments are configured to dynamically move toward and away from each other in response to tension that is applied to the sutures attached to the frame. In response to increased applied tension, the segments are configured to move toward one another relative to the grip, and in response to decreased applied tension, the segments can be configured to move away from one another relative to the grip. The frame optionally includes an indicator configured to provide an indication of the tension applied to the sutures. In this way, as the tension applied to the sutures changes, the indicator indicates the applied tension. The indicated applied tension allows a user of the device to adjust the applied tension until the indicator indicates that the applied tension is at a desired level. The sutures attached to the frame are typically attached to a graft such that the tension applied to the sutures is indicative of a tension applied to the grafts. The indicator is thus be configured to indicate a tension applied to the grafts, which allows the grafts to be tensioned to a desired tension. For example, during performance of a surgical procedure involving soft tissue repair, the grafts can be tensioned to the desired tension and secured at the desired tension to facilitate healing since, as will be appreciated by a person skilled in the art, graft tension affects how well and how quickly the tissue heals (e.g., overly tensioned grafts may be more likely to tear during patient movement after surgery, grafts not tensioned enough may not be in close enough contact to bone when secured thereto to reattach to the bone in a quick and/or strong manner, etc.).

The device is configured to allow a user to hold the device at the grip, either directly (e.g., held by one of the user's hand) or indirectly (e.g., held by a robotic surgical system that is controlled by the user), and apply an even, balanced level of tension to the sutures attached to the frame. The user may thus have at least one hand free while using the device to allow the user to simultaneously manipulate the device with one hand and a surgical instrument with the other hand. This affords a user more control over overall performance of the surgical procedure since the user need not coordinate movement with another user controlling the surgical instrument while the user manipulates the device.

The grip has at least one opening therein, and the at least one opening is configured to enable a surgical instrument to be passed therethrough while the grip is being held by the user. The indicator of the device is positioned so as to be visually observable through the at least one opening regardless of whether or not a surgical instrument is positioned within the opening, thereby allowing the surgical instrument to be in use during tensioning of the sutures attached to the device (and thus during tensioning of the grafts attached to the sutures). The hand of the user holding the grip can be the same hand that holds the surgical instrument positioned within the opening. The user may thus still have one hand free while using the surgical device and the surgical instrument that is advanced through the opening thereof. The user may thus be able to secure sutures during performance of a surgical procedure without being encumbered or slowed down by awkward tools, and/or the user may manipulate a mallet with the free hand not holding the device and instrument and use the mallet to strike the instrument to secure an implant in a bone to thereby hold the tensioned grafts in position relative to the bone.

Figure 2:
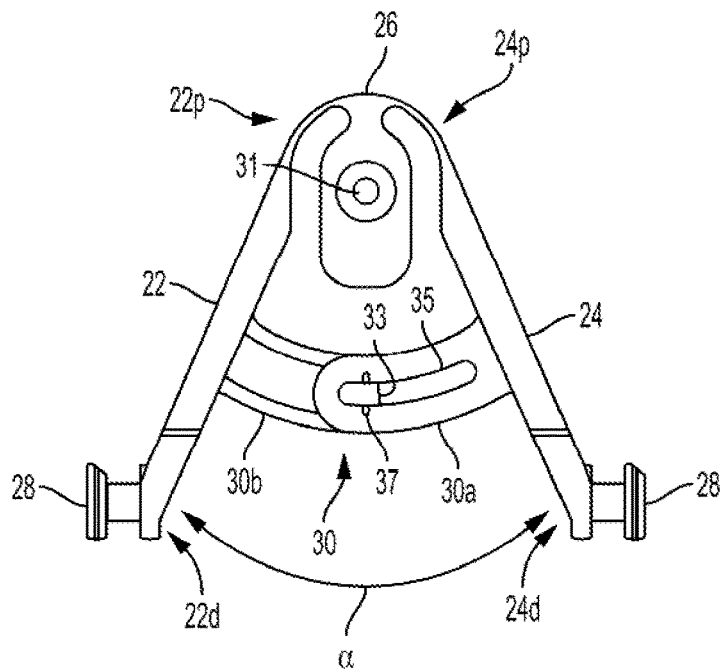
FIG. 2 is a side view of the device of FIG. 1.

FIGS. 1 and 2 illustrate one embodiment of a surgical device 10 for tensioning grafts. Surgical device 10 includes a grip 12 and a frame 20. Grip 12 is configured to be held by a user and it has an opening 14 therein, which is sized and dimensioned to receive a surgical instrument (not shown) therethrough. Frame 20 includes opposed first and second segments 22, 24, which are movably connected to each other and to the grip 12 at proximal ends 22p, 24p thereof by a flexure 26. Distal ends 22d, 24d of each of first and second segments 22, 24 are separated from each other when no tension is applied by the device. Each of first and second frame segments 22, 24 includes at least one suture retention mechanism 28 configured to be removably and replaceably attached to a suture such that a plurality of sutures can be attached to the device 10 via the suture retention mechanisms 28. Device 10 also includes an indicator 30 configured to indicate a tension applied to the sutures attached to the device 10, e.g., attached to the frame 20 via the suture retention mechanisms 28. The grip 12 is configured to fit a human hand. The grip 12 can have a variety of sizes and shapes, for example a length in a range of about 3.5 to 5.5 inches. The opening 14 in the grip 12 can thus have a length that is less than about 5.5. inches, e.g., a length less than about 3.5. inches. The opening 12 can have a variety of sizes and shapes, for example a width in a range of about 0.5 to 1 inches. In general, the size of the opening 12 is configured to accommodate passage of an elongate shaft of a surgical instrument therethrough. The first and second segments 22, 24 can also have a variety of sizes and shapes, such as a length in a range of about 4 to 6 inches and a width (e.g., proximal-distal length between the proximal end 22p and distal end 22d of the first segment 22 and proximal-distal length between the proximal end 24p and distal end 24d of the second segment 24) in a range of about 3.5 to 5 inches.

Grip 12 can have a variety of sizes, shapes, and configurations. In general, the grip 12 is configured to be held by a user during use of the device 10 in a surgical procedure. In an exemplary embodiment, the grip 12 is configured to be held by a single hand of a user during use of the device 10 in a surgical procedure. As in this illustrated embodiment, the grip 12 has an elongate shape configured to be gripped in one hand by a user. In other embodiments, the grip 12 can have another shape, such as a spherical shape, an elliptical shape, a cone shape, a triangular prism shape, etc.

As noted above, grip 12 has an opening 14, which can have a variety of sizes, shapes, and configurations. In general, opening 14 is configured to allow passage of a surgical instrument therethrough, thereby maximizing use of the typically limited amount of surgical space available during performance of a surgical procedure and/or facilitating simultaneous holding of the device 10 and the instrument by a user's hand. Opening 14 is configured to allow user visualization therethrough, which facilitates user visualization of surgical space and/or surgical instruments that would otherwise be obscured by device 10. Opening 14 is configured to simultaneously allow a user to hold the device 10 via grip 12, to manipulate an instrument passed through opening 14 of grip 12, to see the instrument through opening 14, and to observe indicator 30.

While opening 14 has an oval shape in the illustrated embodiment, it can have any of a variety of different shapes, for example a circle, a square, a rectangle, etc. In the illustrated embodiment opening 14 has an elongate shape, which can allow for an instrument to be advanced through opening 14 at any of multiple positions along the length of the elongate opening, thus allowing the instrument to be more comfortably held by a user during use and/or facilitate angular adjustment of the instrument within opening 14. The elongate shape also allows for lateral sliding of an instrument within opening 14, which may facilitate positioning of the instrument relative to a patient.

In the illustrated embodiment opening 14 is in the form of an enclosed hole having a solid perimeter. In other embodiments, opening 14 can be formed in a sidewall of grip 12 as a cut-out therein such that opening 14 is not an enclosed hole. In the event that opening 14 is in the form of a cut-out, it is configured to allow a surgical instrument to slidably advance therethrough while allowing the instrument to be inserted into the opening and removed from the opening by one of either moving the instrument to the side into or out of the opening (e.g., laterally relative to a longitudinal axis of the opening) or moving an end of the instrument into or out of the opening in a vertical fashion (e.g., along the longitudinal axis of the opening) similar to how an instrument can be advanced into and removed from an enclosure hole.

Although opening 14 is shown as a single opening in the illustrated embodiment, in other embodiments, the opening can include multiple openings. Having a single opening may help maximize an amount of visualization possible through grip 12, may provide for more user selection in instrument lateral and angular positions within opening 14, and/or may facilitate manufacturing of grip 12. The use of multiple openings can allow for multiple instruments to simultaneously extend through grip 12, through different ones of the openings with adjacent instruments being separated by a minimum amount of distance defined by a distance between the openings through the adjacent instruments extend. Such a configuration may help prevent instrument interference. The use of multiple openings also allows at least one of the openings to have an instrument extending therethrough and at least one other of the openings to be free of instruments to facilitate visualization through grip 12 (e.g., facilitate unobstructed viewing of indicator 30). The use of multiple openings also allows for at least one of the openings to have a size and shape that corresponds to a particular instrument size and shape (e.g., a round opening having a diameter sized to accommodate an instrument having a circular 7 mm diameter shaft, etc.), which may help a user identify where to advance a particular instrument through grip 12 to maximize effectiveness of the instrument's use with device 10.

As illustrated, opening 14 has empty space therein, e.g., a perimeter thereof defines an empty interior. In other embodiments, opening 14 can have a transparent material disposed therein that allows visualization therethrough. The material can cover the entire opening such that no instrument can be passed therethrough, which may help maintain an area of unobstructed visualization and thereby help prevent indicator 30 from being visually obstructed. The entire coverage of opening 14 may be useful in embodiments of device 10 having multiple openings in grip 12 since one or more of openings 14 can have empty space therein so as to allow instrument passage therethrough while one or more others of openings 14 can have transparent material therein to prevent instrument passage therethrough and to allow visualization therethrough. Alternatively, the material can cover only a part of the opening, which may help indicate to a user where an instrument should be passed through opening 14 since the material prevents instrument passage through part of the opening and/or may help prevent passage of unintended materials like fluid through opening 14.

Figure 3:
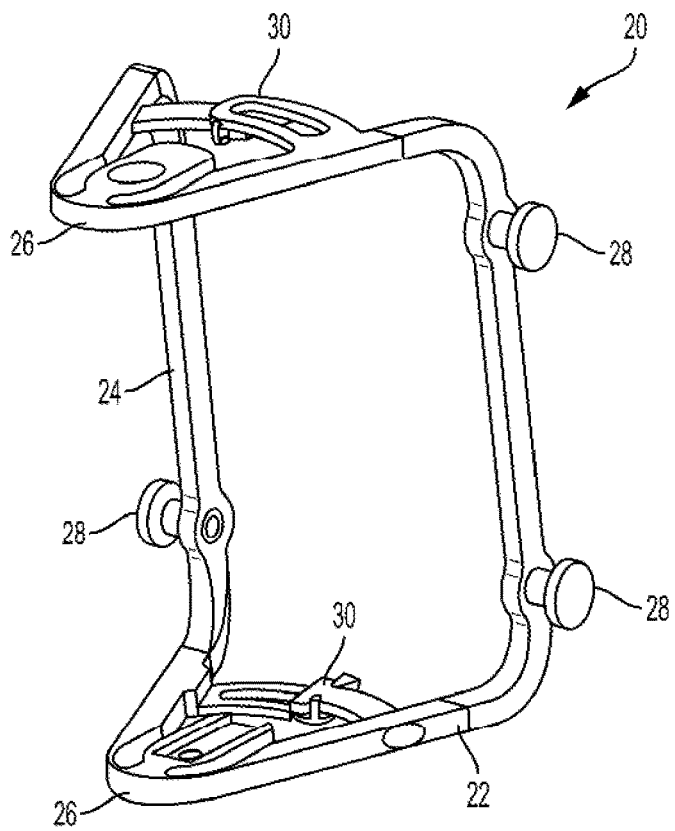
FIG. 3 is a perspective view of a frame of the device in FIG. 1.
Figure 4:
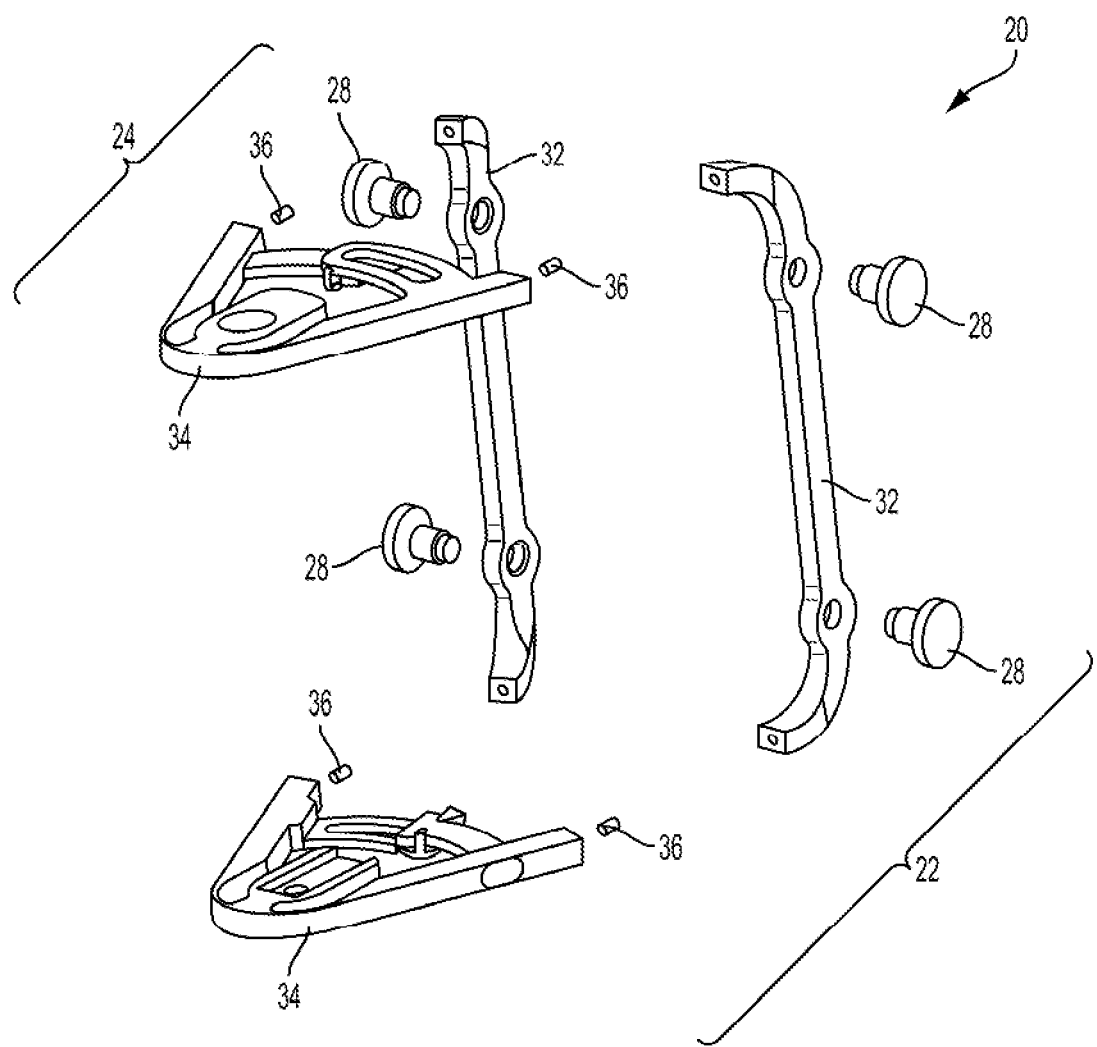
FIG. 4 is an exploded perspective view of the frame of FIG. 3.

Frame 20, which is also shown in FIGS. 3 and 4, can have a variety of sizes, shapes, and configurations. As shown in FIG. 2, frame 20 has an A-shaped cross-sectional shape and it includes first and second segments 22, 24, which can each have a variety of sizes, shapes, and configurations. In the illustrated embodiment, first and second segments 22, 24 are mirror images of one another. Accordingly, frame 20 is symmetrical, which facilitates equal tensioning of sutures attached to the suture retention mechanisms 28 on the segments 22, 24 and hence facilitates equal tensioning of grafts attached to the sutures.

As illustrated in FIGS. 1 and 3, each of first and second segments 22, 24 has a U-shape, which allows for visualization through the interior of the "U" shape into an interior of the overall "A" shape defined by frame 20, thereby facilitating user visualization of surgical space and/or of surgical instruments in use. As shown in FIG. 4, first and second segments 22, 24 of frame 20 can each include a cross beam 32 attached, e.g., by screws 36, to top and bottom flexure members 34 of frame 20. In other embodiments, first and second segments 22, 24 can be formed of different elements and/or assembled in various other ways, such as being formed from single pieces or by being welded, clipped, or bolted together.

As mentioned above, proximal ends 22p, 24p of first and second segments 22, 24 are attached to one another by flexure 26 of frame 20 (e.g., by top and bottom flexure members 34), and distal ends 22d, 24d of first and second segments 22, 24 are spaced apart from one another. Flexure 26 is configured to flex, as discussed further below, such that distal ends 22d, 24d of first and second segments 22, 24 able to move toward and away from one another. In other words, the flexing of flexure 26 causes frame 20 to move relative to grip 12, e.g., cause distal ends 22d, 24d of first and second segments 22, 24 to move towards or away from each other.

Flexure 26 can have a variety of sizes, shapes, and configurations. In general, flexure 26 is configured to dynamically flex in response to a force applied thereto. As in the illustrated embodiment, flexure 26 can be in the form of a living hinge, which facilitates ease of manufacturing and/or durability of the device. In other embodiments, flexure 26 can have another configuration, such as a spring (e.g., a coil spring, a volute spring, etc.), an elastic band or other elastic member, etc. Flexure 26 can be fabricated in any of a variety of ways, such as by machining, punching, molding, wiring, etc.

Flexure 26 is also configured to provide a biasing force to first and second segments 22, 24 to bias first and second segments 22, 24 away from one another, e.g., bias distal ends 22d, 24d of first and second segments 22, 24 away from one another. When tension applied to sutures attached to frame 20 exceeds the biasing force, flexures 26 flex and thereby cause segments 22, 24 to move towards each other, as discussed further below.

As shown in FIG. 2, frame 20 has a window 31 formed therein adjacent to flexure 26. Thus, in the illustrated embodiment, which includes two flexures 26 (a top flexure 26 and a bottom flexure 26), the frame 20 has two windows. In other embodiments, frame 20 can include another number of windows therein. In general, window 31 is configured to allow visual access therethrough, similar to opening 14 discussed above, and can either be empty space or have transparent material disposed therein, also similar to that discussed above regarding the opening 14. The positioning of window 31 adjacent the flexure 26 enables positioning of window 31 adjacent grip 12, as shown in FIGS. 1 and 2, which enables visualization of an instrument positioned within the opening 14.

As also shown in FIG. 2, distal ends 22d, 24d of segments 22, 24 define a variable angle α. FIG. 2 illustrates the device in a condition in which no tension is applied and angle α is at a maximum. When tension is applied, such as by tensioning sutures/grafts attached to segments 22, 24, angle α will decrease as segments 22, 24 move towards each other. As further illustrated in FIG. 2, first segment 22 includes a first extension 30a extending radially inward therefrom toward second segment 24. Second segment 24 likewise includes a second extension 30b extending radially inward therefrom toward first segment 22. First and second extensions 30a, 30b thus define the crossbar of the frame's "A" shape. First and second extensions 30a, 30b are movably coupled to one another such that in response to flexing of flexure 26, and changing angle α, first and second extensions 30a, 30b move relative to one another. Such movement of first and second extensions 30a, 30b can facilitate use of indicator 30 to indicate an amount of tension applied to sutures attached to the frame 20, as discussed further below. In the illustrated embodiment, first segment 22 includes two first extensions 30a and second segment 24 includes two second extensions 30b, each one associated with one of the first extensions 30a, as shown in FIG. 1. Top extensions 30a, 30b are associated with top flexure 26, and bottom extensions 30a, 30b are associated with bottom flexure 26.

Indicator 30 can have a variety of sizes, shapes, and configurations as long as it is able to provide an indication of an amount of tension applied to sutures attached to the device 10 and hence the tension applied to grafts attached to the sutures. By coupling indicator 30 to frame 20, as described herein, movement of frame 20 in response to the tension applied to the sutures will cause the indicator 30 to indicate a different magnitude of tension depending on the relative position of the extensions 30a, 30b. A user of device 10 can thus observe indicator 30 and quickly assess the magnitude of the tension applied to the sutures and hence the grafts attached thereto. Such a configuration enables an accurate and efficient technique for applying the desired amount of tensioned to grafts during a surgical procedure.

In the illustrated embodiment, indicator 30 includes a mark on one of the segments 22, 24 and a window 35 in the other of segments 22, 24 through which the mark can be observed. A position of the mark within the window is indicative of the tension being applied. As shown in FIG. 2, first segment 22 includes a mark 33 while second segment 24 includes a window 35 through which mark 33 can be visualized. Mark 33 and window 35 are included on second and first extensions 30b, 30a, respectively, of second and first segments 24, 22 such that mark 33 and window 35 are configured to move relative to one another in response to the flexing of flexure 26. As illustrated, mark 33 includes a straight line printed on first segment 22 and window 35 includes a pair of opposed slits formed in second segment 24. A notch 37 is formed across window 35 such that corresponding ends of notch 37 oppose each other on the opposed slits of window 35. Mark 33 and notch 37 are configured to be aligned with one another in response to a predetermined force being applied to sutures attached to the frame 20, the predetermined force being greater than the bias force biasing segments 22, 24 apart from one another. Thus, when segments 22, 24 have moved a predetermined distance in response to the predetermined force, mark 33, visible through window 35, will be aligned with notch 37 so as to indicate that the sutures (and the grafts attached thereto) are at the predetermined force. A person skilled in the art will appreciate that indicator 30 can have other configurations. For example, a mark of indicator 30 can include a dot, a linear groove, a number, etc. formed in one of segments 22, 24, etc. configured to align with a window of the other segment. For another example, indicator 30 can include a mark on second segment 24 configured to align with a mark on first segment 22. For yet another example, indicator 30 can include a dial that moves in response to movement of the frame 20.

As in the illustrated embodiment, indicator 30 can be configured to indicate a single predetermined tension. In other words, alignment of mark 33 and notch 37 indicates that the predetermined tension is being applied. Otherwise, when mark 33 and notch 37 are not aligned, it will be evident that the tension being applied is less than or greater than the predetermined tension.

In other embodiments indicator 30 can be configured to indicate any one of a plurality of predetermined tensions. Device 10 may thus have versatility of use since it can be configured to indicate different tensions, each of which may be preferred by different surgeons and/or be appropriate for different patients and/or different types of surgical procedures. For example, a plurality of marks can be used, each being at a different axial position along the segment that includes the marks, e.g., at a different axial position along the extension that includes the mark. Each of the marks can correspond to a different predetermined tension such that when a one of the marks is aligned with the window on the other segment, the sutures (and grafts attached thereto) are known to have that mark's predetermined tension applied thereto. For another example, instead of a single window, a plurality of windows can be used, each being at a different position along the segment that includes the windows, e.g., at a different position along the extension that includes the windows. Each of the windows can correspond to a different predetermined tension such that when a one of the windows is aligned with the mark on the other segment, the sutures (and grafts attached thereto) attached to device 10 can be known to have that window's predetermined tension applied thereto.

The predetermined tension(s) to be indicated by indicator 30 can be any of a variety of tension levels. In an exemplary embodiment, the predetermined tension(s) can each be in a range of about 10 to 30 pounds, e.g., about 12 pounds, about 15 pounds, etc. A person skilled in the art will appreciate that the indicator need not enable a precise magnitude of tension to be determined. Rather, the purpose of the indicator is to provide an approximate indication of the applied tension.

As described herein indicator 30 includes two indicators; a top indicator 30 associated with top flexure 26 and a bottom indicator 30 associated with bottom flexure 30. The use of top and bottom indicators facilitates visualization of the indicator 30 regardless of whether grip 12 is being held with a left hand of a user or a right hand of the user since one of the two indicators will always be "face up" and/or regardless of an angular orientation at which the user is holding the device since at least one of the indicators should be viewable. In the illustrated embodiment, the top and bottom indicators are identical, which facilitates ease of manufacturing and/or user understanding of indicator functionality. One skilled in the art will understand, however, that when two or more indicators are included, any one of the indicators may differ from any of the other indicators. For example, a top indicator may be configured to indicate a first predetermined tension, and a bottom indicator may be configured to indicate a second, different predetermined tension. For another example, one indicator may use a first color and another indicator may use a second color that may have better contrast that the fist color under certain lighting conditions.

In the embodiment illustrated, indicator 30 is viewable on an exterior of device 10, but not on an interior of the device. For example, the top indicator 30 is viewable, as shown in FIG. 1, but the bottom indicator 30 is not viewable since the bottom exterior surface of the device is not visible in the illustration. In other embodiments, indicator 30 can be viewable on both an interior and an exterior of device 10, e.g., there can be four indicators 30 (top exterior, top interior, bottom exterior, bottom interior). The presence of an indicator on both the device's interior and exterior may allow the indicator to be visible through the opening 14 by allowing visualization therethrough of the interior indicator.

Suture retention mechanisms 28 can have a variety of sizes, shapes, and configurations. In general, each of the suture retention mechanisms can be configured to have a suture removably and replaceably attached thereto so as to attach sutures to frame 20. Each suture retention mechanism 28 can be configured to attach to any number of sutures, e.g., one, two, three, etc. Each of first and second segments 22, 24 can include an equal number of suture retention mechanisms 28, which may allow for balanced tension to be applied to frame 20 via the sutures. Suture retention mechanisms 28 can be positioned on first and second segments 22, 24 in a mirror image relationship with respect to one another, as in the illustrated embodiment in which the top two suture retention mechanisms 28 on frames 22, 24 nearest top flexure 26 are at mirrored positions and the bottom two suture retention mechanisms 28 on frames 22, 24 nearest bottom flexure 26 are at mirrored positions. Suture retention mechanisms 28 can thus be arranged on frame 20 such that pairs of corresponding suture retention mechanisms 28 can be positioned opposite to each other on opposite first and second segments 22, 24.

While suture retention mechanisms 28 are shown to be in the form of pegs configured to have a suture wrapped and/or tied therearound, the suture retention mechanisms can have various other configurations, such as hooks, clips, spring-loaded pins, etc. Suture retention mechanisms 28 in the illustrated embodiment are passive in that they are not movable to actively lock any sutures coupled thereto. Instead, suture retention mechanism 28 holds the sutures that are wrapped or tied therearound. In other embodiments, suture retention mechanisms 28 can be active in that they are movable to lock and unlock sutures attached thereto.

In the illustrated embodiment, the grip 12 and the frame 20 are non-removably attached together, e.g., by welding, adhesive, etc. In other embodiments, the frame can be configured to removably attach to the grip, e.g., by a snap fit or other connection to the grip. Such a configuration enables the frame to be removed from the grip and disposed of after use while the grip can be reused (after appropriate cleaning, etc.) with a new frame attached thereto.

Various materials can be used to form grip 12 and frame 20, including metal, plastic, or a combination thereof. The grip 12 can be made of one material, such as a metal, while the frame 20 can be made of another material, such as plastic. Exemplary metals include stainless steel and nitinol, aluminum, and composites including for example carbon fiber composite, while exemplary plastics include polyethylene, polypropylene, and polycarbonate, and acrylonitrile butadiene styrene (ABS) nylon.

As mentioned above, a surgical device for tensioning grafts can be configured to be held by a user, either by the user manually holding the grip or by having the grip being coupled to a robotic surgical system that is controlled by the user. Exemplary embodiments of robotic surgical systems that can be used with any of the surgical devices disclosed herein are described in more detail in U.S. Pat. Pub. No. 2012/0158013 filed Jun. 21, 2012 and entitled "Surgical System and Methods for Mimicked Motion" U.S. patent application Ser. No. 14/827,601 filed Aug. 17, 2015 and entitled "Gathering and Analyzing Data for Robotic Surgical Systems," which are incorporated herein by reference in their entireties.

As mentioned above, a surgical device for tensioning grafts can be used in any of a variety of surgical procedures. Exemplary procedures include soft tissue repair procedures in which soft tissue is anchored to bone such as in anterior cruciate ligament (ACL) repairs and in rotator cuff repairs. Exemplary embodiments of surgical procedures involving graft tensioning in which the graft tensioning devices disclosed herein can be used are described in U.S. Pat. No. 8,435,293 entitled "Flexible Tibial Sheath" issued on May 7, 2013, U.S. Pat. No. 8,226,714 entitled "Femoral Fixation" issued on Jul. 24, 2012, and in U.S. Pat. No. 6,554,862 entitled "Graft Ligament Anchor And Method For Attaching A Graft Ligament To A Bone" issued on Apr. 29, 2003, which are hereby incorporated by reference in their entireties.

Figure 5:
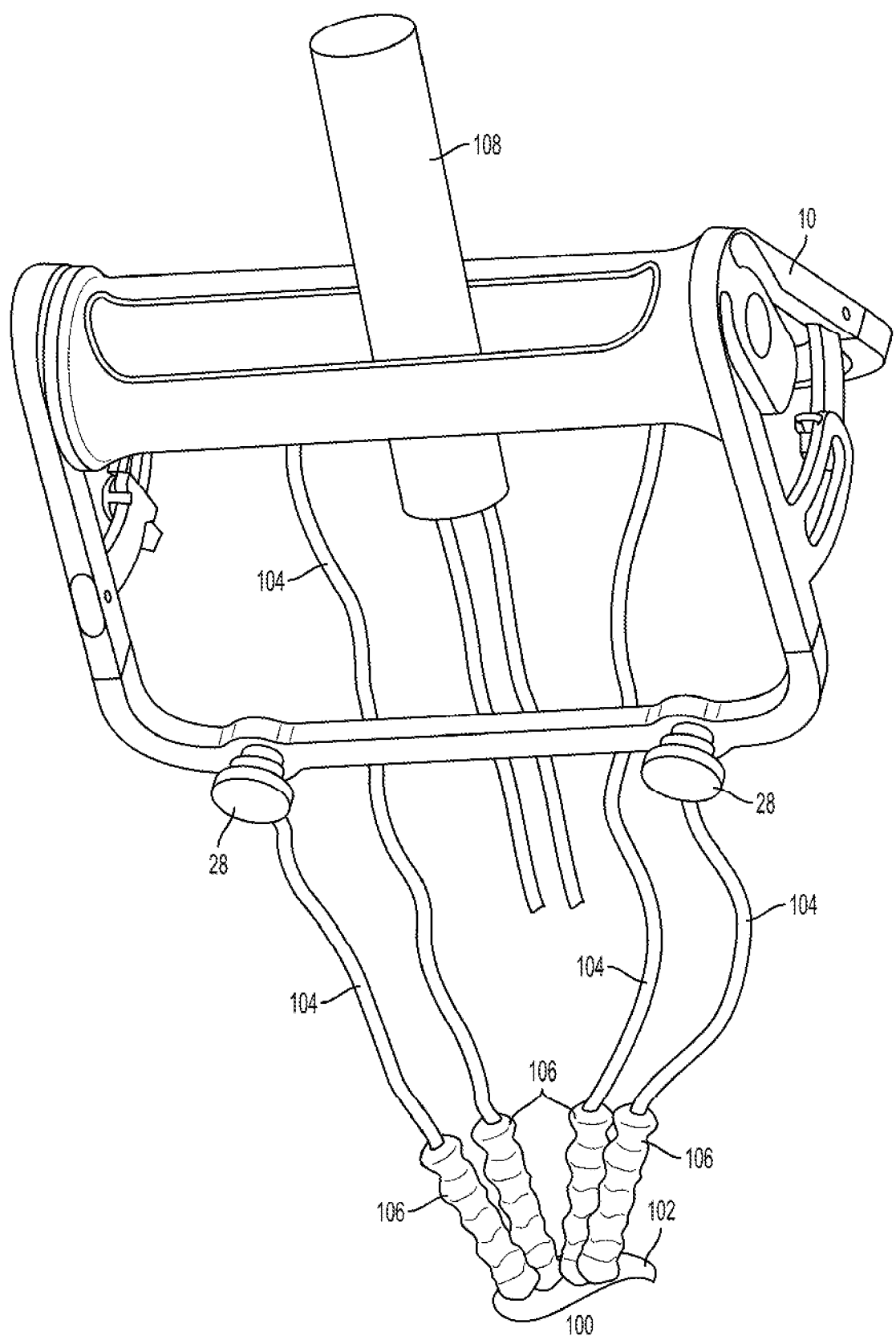
FIG. 5 is a perspective view of the device of FIG. 1 in one embodiment of use.

FIG. 5 illustrates one embodiment of using graft tensioning device 10 of FIG. 1 during a surgical procedure. Although FIG. 5 describes a procedure using device 10 of FIG. 1, it is understood that the procedure can be performed using a different surgical device described herein for tensioning grafts.

To attach soft tissue to bone 100, a bore, bone hole, or bone tunnel can be formed in bone of a patient. The bone hole can be pre-formed, such as by using a drill, an awl, a punch instrument, etc., as will be appreciated by a person skilled in the art. Alternatively, the bone hole can be formed simultaneously with advancement of a suture anchor into the bone and simultaneously with engagement of the anchor therewith, such as by using a self-awling or self-tapping driver and/or self-awling or self-tapping anchor.

FIG. 5 illustrates four sutures 104 coupled to the anchor 102 before or after a bone hole is formed in the bone 100. Sutures 104 are coupled to the soft tissue (e.g. a graft strand) 106 prior to sutures 104 being coupled to the anchor 102. One of a plurality of graft strands 106 is coupled to each of the sutures 104 such that four graft strands 106 are coupled to the device 10 via sutures 104, which are attached to the suture retention mechanisms 28 (two of which are obscured in FIG. 5) either before or after the soft tissues 106 are attached thereto.

A driver tool 108 is advanced through the opening 14 of the device 10 to drive the anchor 102 (which has sutures 104 coupled thereto) into bone 100. For clarity of illustration, a distal end of driver tool 108 is not illustrated in FIG. 5. Prior to driving anchor 102 into bone 100, however, sutures 104 and graft strands 106 coupled to anchor 102 are tensioned to place the graft strands 106 in an optimal position relative to the bone by pulling the sutures 104, and hence pulling the graft strands 106 attached thereto, in a direction away from anchor 102 and bone 100. As the anchor 102 is driven into bone 100, the tension is maintained by device 10 by sustaining the desired tension as indicated by the indicator 30. A mallet (not shown) or other tool is used to further advance driver tool 108 distally to drive anchor 102 into bone 100. One of a user's hands holds grip 12 of device 10 and instrument 108 positioned within opening 14 while the user's other hand can operate the mallet or other tool. Alternatively, one user can hold device 10 and another user can operate the mallet or other tool.

With anchor 102 driven into bone 100, sutures 104 and soft tissues 106 are held in place relative to bone 100 to facilitate healing.

In various embodiments, sutures 104 can each be a single strand or can be multi-stranded, and can be either folded or unfolded. Graft strands 106 can be coupled to sutures 104 by passing the sutures 104 through graft strands 106 before or after sutures 104 are coupled to anchor 102. Driver tool 108 can also include any of a variety of driver tools as will be appreciated by a person skilled in the art.

Figure 6:
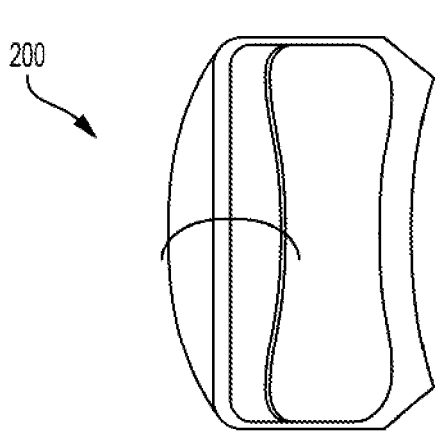
FIG. 6 is a side view of one embodiment of a tensioning device.
Figure 7:
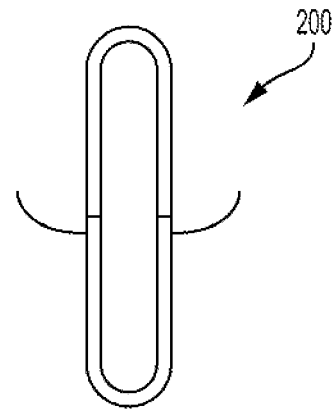
FIG. 7 is a top-down view of the tensioning device of FIG. 6.

FIGS. 6-22 illustrate various embodiments of frames and grips that can be incorporated into any of the embodiments described above. FIGS. 6-7 illustrate another embodiment of a surgical device 200 that includes a grip and a frame. FIG. 6 illustrates the grip having an outer curved profile configured to rest comfortably against a palm of a hand. FIG. 7 shows an opening in the grip configured to allow passage of a surgical instrument therethrough. The opening in this illustrated embodiment has an elongate oval shape.

Figure 8:
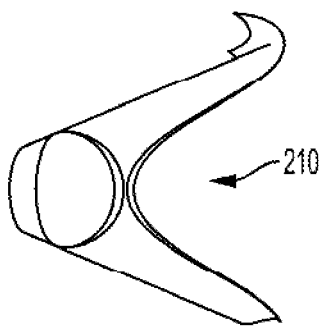
FIG. 8 is an end view of a portion of one embodiment of a tensioning device.
Figure 9:
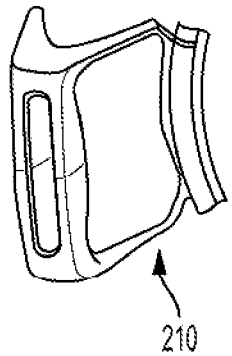
FIG. 9 is a perspective view of the tensioning device of FIG. 8.
Figure 10:
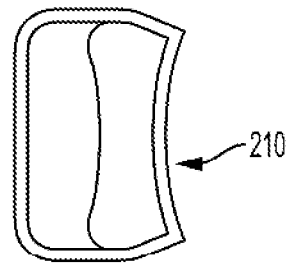
FIG. 10 is a side view of the tensioning device of FIG. 8.

FIGS. 8-10 illustrate another embodiment of a surgical device 210 that includes a grip and a frame. As shown in FIGS. 8 and 9, a distal end of each of the first and second segments of the frame has a curved profile defining a hook configured as a suture retention mechanism. As shown in FIGS. 9 and 10, the grip has an inner curved profile configured to be gripped by fingers of a person's hand.

Figure 11:
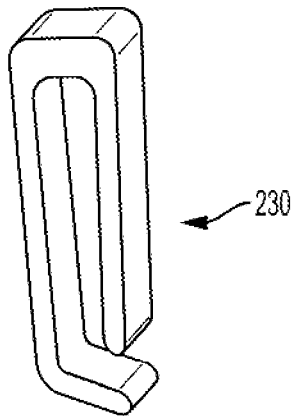
FIG. 11 is a perspective view of yet another embodiment of a grip of a tensioning device.

FIG. 11 illustrates another embodiment of a grip 230. The grip 230 in this illustrated embodiment has an opening therein that is not in the form of an enclosed hole. Instead, as discussed above, the opening is configured to allow a surgical instrument to slidably advance therethrough while allowing the instrument to be inserted into the opening and removed from the opening by moving the instrument to the side into or out of the opening (e.g., laterally relative to a longitudinal axis of the opening). The opening has an instrument entry/exit at a bottom end thereof.

Figure 12:
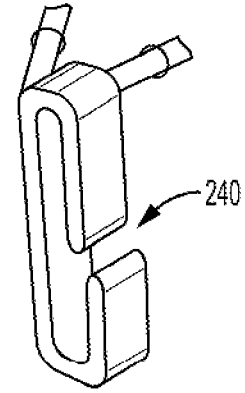
FIG. 12 is a perspective view of a portion of still another embodiment of a surgical device.

FIG. 12 illustrates another embodiment of a surgical device 240 that includes a grip and a frame. The grip in this illustrated embodiment is similar to the grip 230 of FIG. 11 in that an opening formed therein is not in the form of an enclosed hole and is configured to allow a surgical instrument to slidably advance therethrough while allowing the instrument to be inserted into the opening and removed from the opening by moving the instrument to the side into or out of the opening. The opening has an instrument entry/exit in an intermediate portion thereof that is substantially at a midpoint along a length of the opening.

Figure 13:
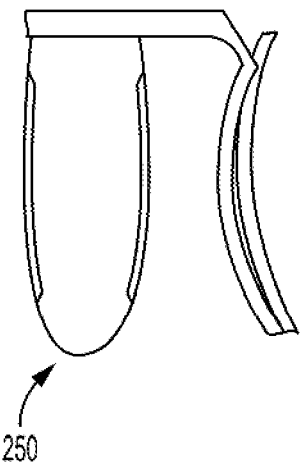
FIG. 13 is a side view of another embodiment of a tensioning device.
Figure 14:
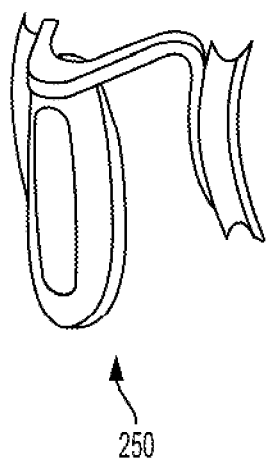
FIG. 14 is a perspective view of the device of FIG. 13.

FIGS. 13-14 illustrate another embodiment of a surgical device 250 that includes a grip and a frame. The frame has an open bottom side, e.g., only has segments at a top thereof. The grip has an opening in the form of an enclosed hole.

Figure 15:
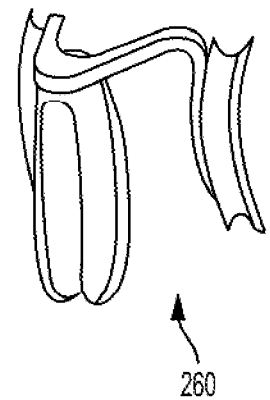
FIG. 15 is a perspective view of yet another embodiment of a tensioning device.

FIG. 15 illustrate another embodiment of a surgical device 260 that includes a grip and a frame. The frame has an open bottom side similar to the frame of FIGS. 13 and 14. The grip has an opening formed therein is not in the form of an enclosed hole, similar to the openings of FIGS. 11 and 12. In this illustrated embodiment, the opening is configured to allow a surgical instrument to slidably advance therethrough while allowing the instrument to be inserted into the opening and removed from the opening by moving an end of the instrument into or out of the opening in a vertical fashion (e.g., along the longitudinal axis of the opening).

Figure 16:
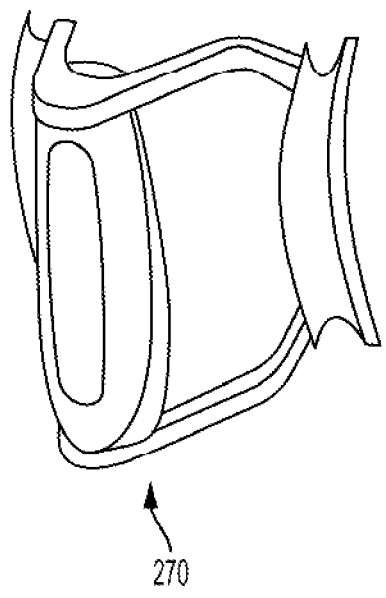
FIG. 16 is a perspective view of another embodiment of a tensioning device.
Figure 17:
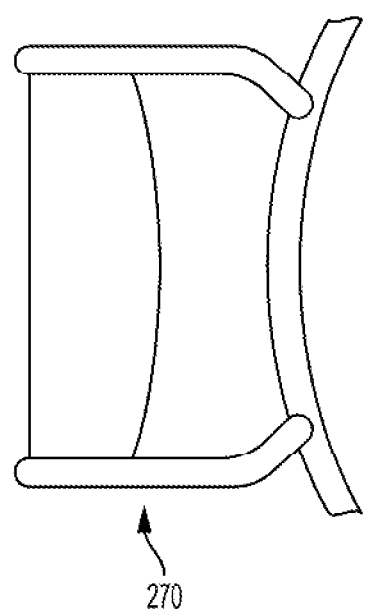
FIG. 17 is a side view of the tensioning device of FIG. 16.

FIGS. 16-17 illustrate another embodiment of a surgical device 270 that includes a grip and a frame. The grip has a curved inner surface similar to the grip of FIG. 10.

FIGS. 18-19 illustrate another embodiment of a surgical device 280 that includes a grip and a frame. The grip includes two balls with open space therebetween. Either one of the balls can be handheld for manipulation of the device, which may facilitate right and left handed use of the device. Alternatively, both of the balls can be handheld for manipulation of the device.

FIG. 20 illustrates another embodiment of a surgical device 290 that includes a grip and a frame. The frame includes a suture retention mechanism at a distal end of each of its segments for a total of four suture retention mechanisms. Each of the suture retention mechanisms face radially outward.

As mentioned above, a surgical device for tensioning grafts can be used in any of a variety of surgical procedures. FIG. 21A illustrates one embodiment of four graft strands in a bone hole, two semitendinosus strands (the top two circles in the bone hole) and two gracilis strands (the bottom two circles in the bone hole) prior to tensioning thereof. Each of the graft strands can be attached to a tensioning device as described herein, and the graft strands can be tensioned using the device. FIG. 21B illustrates the four graft strands after the tensioning.

FIG. 21C illustrates one embodiment of two graft strands in a bone hole, two semitendinosus strands prior to tensioning thereof. Each of the graft strands can be attached to a tensioning device as described herein, and the graft strands can be tensioned using the device. FIG. 21D illustrates the two graft strands after the tensioning.

In various embodiments, a single graft strand, for example an Achilles tendon graft, can be coupled to a plurality of sutures that are then coupled to a graft tensioning device and tensioned similar to that discussed above.

A person skilled in the art will appreciate that the implementations described herein have application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device," incorporated herein by reference in its entirety. It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   coupling a plurality of graft strands to a plurality of suture retention members of a graft tensioning device, the plurality of graft strands being at a first tension when coupled to the graft tensioning device; and
   applying a tension force to the graft strands through the tensioning device, the tension force causing first and second frames of the tensioning device to dynamically flex to change a variable angle between the first and second frames at a flexure coupling the first and second frames together, the tension force causing the plurality of graft strands to change from being at the first tension to being at a second tension, and the graft tensioning device including an indicator that indicates that the plurality of graft strands are at the second tension.

2. The method of claim 1, wherein the indicator is configured to indicate any one of a plurality of predetermined tensions, the second tension being one of the predetermined tensions.

3. The method of claim 1, further comprising advancing a surgical instrument through a passageway of the graft tensioning device.

4. The method of claim 3, further comprising advancing the surgical instrument through at least one enclosed hole within the passageway.

5. The method of claim 3, further comprising advancing the surgical instrument through at least one cut-out in a sidewall of the passageway of the graft tensioning device.

6. The method of claim 1, wherein the indicator includes first and second indicators, and a relative positioning of the first indicator and the second indicator provides the indication of the tension applied to the plurality of graft strands.

7. The method of claim 1, wherein the flexure biases distal ends of the first and second frames away from one another, and applying the tension force to the graft strands through the tensioning device comprises overcoming the bias of the flexure to move the distal ends of the first and second frames toward one another.

8. A surgical method, comprising:
removably securing a plurality of sutures to a plurality of suture retention members on first and second portions of a graft tensioning device, proximal ends of the first and second portions being coupled together by a plurality of hinges, the plurality of hinges biasing distal ends of the first and second portions away from one another in a first position; and
applying a tension force to the plurality of sutures through the tensioning device, the tension force overcoming the bias of the plurality of hinges and causing the distal ends of the first and second portions of the graft tensioning device to move toward one another from the first position into a second position.

9. The method of claim 8, further comprising advancing a surgical instrument through a passageway of the graft tensioning device.

10. The method of claim 9, further comprising advancing the surgical instrument through at least one enclosed hole within the passageway.

11. The method of claim 9, further comprising advancing the surgical instrument through at least one cut-out in a sidewall of the passageway of the graft tensioning device.

12. The method of claim 8, wherein an indicator on the graft tensioning device indicates that the plurality of sutures has achieved a preset tension level in response to the applied tension force.

13. The method of claim 8, wherein the plurality of sutures move from a lower first tension to a higher second tension to overcome the bias of the plurality of hinges in response to the applied tension force.

14. The method of claim 8, wherein each of the plurality of hinges includes a living hinge.

\* \* \* \* \*